United States Patent
Fischer

(10) Patent No.: US 8,157,752 B2
(45) Date of Patent: Apr. 17, 2012

(54) POSTURE ASSESSMENT AND FEEDBACK INSTRUMENT

(76) Inventor: Peter Fischer, Tuebingen (DE)

( * ) Notice: Subject to any disclaimer, the term of this patent is extended or adjusted under 35 U.S.C. 154(b) by 373 days.

(21) Appl. No.: 12/542,746

(22) Filed: Aug. 18, 2009

(65) Prior Publication Data

US 2011/0046518 A1    Feb. 24, 2011

(51) Int. Cl.
*A61B 5/117* (2006.01)
*A61B 5/103* (2006.01)

(52) U.S. Cl. ........................................................ 600/594

(58) Field of Classification Search .................. 600/300, 600/301, 587, 595, 594; 601/71; 33/512, 33/1 N; 324/660, 686, 71.1; 473/274; 482/148, 482/909; 340/573.7; 377/24.2
See application file for complete search history.

(56) References Cited

U.S. PATENT DOCUMENTS

| | | | |
|---|---|---|---|
| 4,007,733 A | 2/1977 | Celeste |
| 5,143,088 A | 9/1992 | Marras |
| 5,433,201 A | 7/1995 | Manthey |
| 5,533,531 A | 7/1996 | Edwards |
| 6,673,027 B2 | 1/2004 | Fischer |
| 6,827,694 B2 | 12/2004 | Gladoun |
| 6,877,240 B2 | 4/2005 | Tranas |
| 7,565,295 B1 | 7/2009 | Hernandez-Rebollar |
| 2008/0319364 A1 | 12/2008 | Josey |

*Primary Examiner* — Brian Szmal

(57) ABSTRACT

A posture assessment and feedback instrument (FIG. 1A and FIG. 1B) all contained within a single housing (1). The output of a capacitive sensor (4) within the housing (1) varies in response to the distance between the sensor and the body of a user. The housing (1) is strapped to the body of a user (FIG. 3, FIG. 4, FIG. 5A, and FIG. 5B) with a belt (2). The application area is chosen such that the distance between the sensor (4) and the body varies in response to a defined posture change (FIG. 5A and FIG. 5B). Thus the sensor output will vary in response to the defined posture change. The output is compared to a stored threshold value and triggers a feedback signal when the threshold is exceeded.

16 Claims, 4 Drawing Sheets

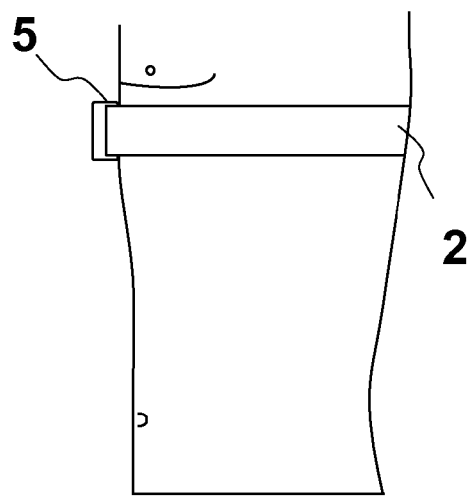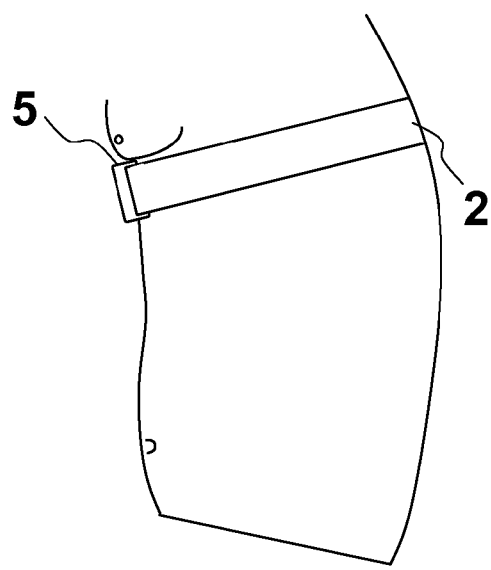
Fig. 5A                    Fig. 5B

POSTURE ASSESSMENT AND FEEDBACK INSTRUMENT

BACKGROUND

1. Field of Invention

This invention relates to posture assessment and feedback instruments that respond to bending and curvature.

2. Description of Prior Art

This invention relates to a posture feedback instrument designed to prevent slumped posture and the associated ailments. In order to achieve this task successfully, a posture feedback instrument needs to be reliable, user-friendly, inexpensive and durable. A single inclination sensor as used in U.S. Pat. No. 6,877,240 (2005) cannot differentiate slumping from leaning forward with a straight back, while a multitude of sensors would make the process expensive and less user-friendly. Therefore, a reliable assessment of slumped posture requires a sensor that is sensitive to curvature rather than inclination.

Amongst the curvature sensing prior art, U.S. Pat. No. 6,673,027 (2004) was turned into a commercially available posture feedback instrument. Studies showed it to function reliably and effectively. It is also user-friendly in the sense that its application to the xyphoid area can be accomplished independently and does not impede activities of daily living such as leaning against a back rest.

The main deficiencies of the embodiment of U.S. Pat. No. 6,673,027 are caused by the design of its sensor. The sensor is composed of a signal source and a receiver element connected by a moveable hardware component. Manufacturing the moveable hardware component with the required precision turned out to be a complex and costly process. The moveable component has also turned out to be the least durable one. It is the only part that has ever required replacement after breaking in a number of cases. Its fragility also made it less user-friendly, because it required the users to read the manual and treat the sensor with care. Finally, cleaning moveable components for functional, aesthetic, and cleaning purposes is cumbersome.

Therefore, a curvature sensing solution was sought in which the user-friendly and effective application of a single sensor to the xyphoid area could be preserved, while eliminating the moveable hardware component.

The solution was found by replacing the separate signal source and the moveable hardware component of U.S. Pat No. 6,673,027 with a capacitive sensor. A typical capacitive sensor creates an electric field between two metal traces on a piece of circuit board. When the field is invaded by a human body, the sensor output changes according to how close the body gets. This makes the proximity of the body the input variable, rather than the distance between a signal source and a receiver. Thus a capacitive sensor eliminates the need for a signal source that can move in relation to its receiver.

The only prior art use of a capacitive sensor in the context of posture assessment was found in the sign language recognition apparatus of U.S. Pat. No. 7,565,295 (2009), where a capacitive sensor as a part of an accelerometer was used to measure the acceleration of the signing fingers rather than their curvature.

No prior art was found in which the sensing means for curvature of the spine or other joints was capacitive.

The alternative sensing means used for this purpose in the prior art all suffer from at least one of the following disadvantages:

Sensing means like the ones used in U.S. Pat. No. 5,433, 201 (1995) require a receiver and a separate signal source. In order to power the separate signal source, it needs to be connected to the power source via a cable. The separate signal source and the cable connection complicate the handling and the production of the sensing means.

Sensing means like the ones used in U.S. patent application 20080319364 (2008), U.S. Pat. No. 6,673,027 (2004), U.S. Pat. No. 5,143,088 (1992) or U.S. Pat. No. 4,007,733 (1977) require a moveable piece of hardware, compromising the durability of the sensor and making it more difficult to clean. The moveable piece of hardware needs to be crafted with precision, so that it will move easily but without slack, thus adding to production costs.

Sensing means like the ones used in U.S. Pat. No. 5,433, 201 (1995) may only be applied to the skin and won't function when applied to the clothes, where the operation and demonstration of sensing means is easier and where there is less sweating between a sensor and the body.

Sensing means like the ones used in U.S. Pat. Nos. 5,433, 201 (1995), 6,673,027 (2004) or 5,533,531 (1996) do not allow an embodiment where the entire posture feedback instrument is contained within a single housing.

Sensing means like the ones used in U.S. Pat. Nos. 6,827, 694 (2004) or 5,143,088 (1992) do not allow a user-friendly application to the xyphoid area, where it can be reached and handled by a user, while not being in the way when using a back rest.

OBJECTS AND ADVANTAGES

Accordingly, several objects and advantages of applying only a single capacitive sensor with no moveable components to the xyphoid area for the assessment of slumped posture as proposed in the present invention are:

that it makes a separate signal source redundant thus facilitating production, cleaning, and handling;

that the sensor is free of fragile components, thus improving its durability;

that a capacitive sensor may be separated from the skin of a user by a layer of clothes. This allows an optional application to the clothes, where the operation and demonstration of the sensor is easier and where there is less sweating between the sensor and the body;

that a capacitive sensor may be separated from the skin of a user by a layer of plastic. This allows the capacitive sensor to be mounted within the same plastic housing that also holds its power source and a feedback unit. Thus a wireless embodiment of a posture feedback instrument all contained in a single housing becomes feasible;

that it allows a user-friendly application to the xyphoid area, where it can be reached and handled by a user while not being in the way when using a back rest.

BRIEF SUMMARY OF THE INVENTION

In accordance with the present invention a method for assessing the posture of a user comprises (a) choosing a sensor that provides an output in response to the distance between the sensor and the body of the user, (b) choosing a suitable area of the user's body having properties causing the mentioned distance to vary in response to a defined posture change, (c) applying the sensor to that area, causing the mentioned distance and thus the output of the sensor to vary in response to the defined posture change, and (d) the option of alerting the user whenever a defined posture threshold is exceeded.

The preferred sensor is a capacitive sensor. The output of the sensor varies in response to the distance between the sensor and the body of a user. This eliminates the need for the separate signal source and moveable connections of prior art sensing means, thus solving the associated drawbacks concerning their handling, cleaning, durability and production.

BRIEF DESCRIPTION OF THE SEVERAL VIEWS OF THE DRAWING

FIG. 5A shows a side view of a user in upright posture wearing the posture assessment instrument.

FIG. 5B shows a side view of the same user as in FIG. 5 only this time in slumped posture.

Figure 1A:
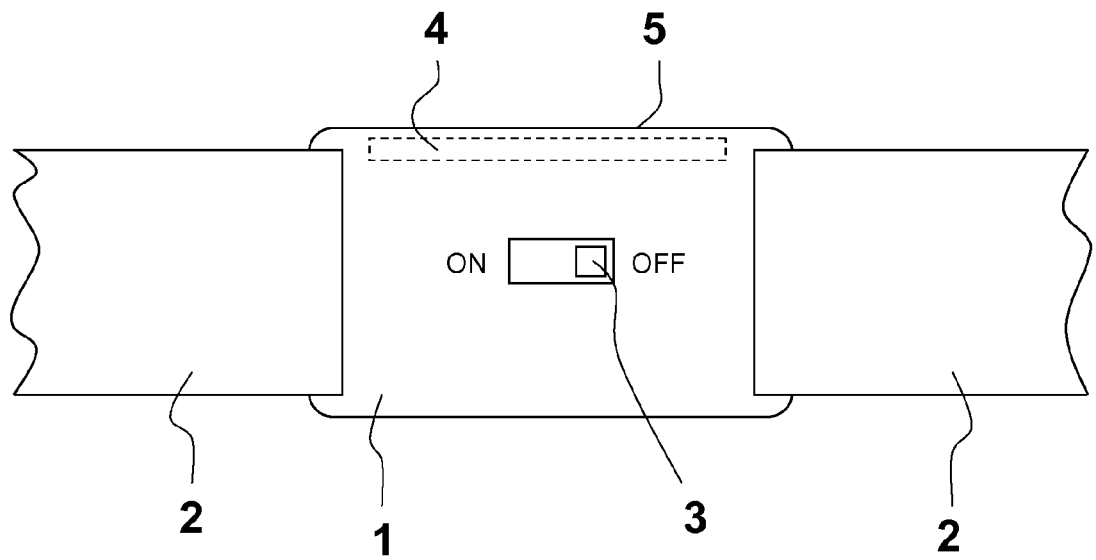
FIG. 1A shows a front view of the preferred embodiment of the posture assessment instrument.
Figure 1B:
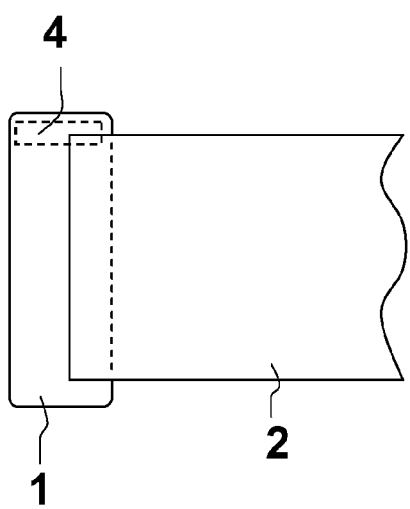
FIG. 1B shows a side view of the preferred embodiment of the posture assessment instrument.

BRIEF DESCRIPTION OF THE REFERENCE NUMERALS OF THE DRAWING 1 housing
2 belt
3 switch
4 capacitive sensor
5 top of housing
6 pressure-sensitive foil
7 back of housing Detailed Description of the Invention The preferred embodiment of the posture assessment and feedback instrument of the present invention is illustrated in FIG. 1A and FIG. 1B, showing the single housing 1 in which all the necessary electronic components and their power source are contained. The housing is attached to a belt 2. A switch 3 in the center of the housing 1 allows the instrument to be turned on and off. A capacitive sensor 4 is attached to the bottom side of the top of the housing 5. The capacitive sensor 4 is connected to a circuit board containing a microprocessor and a feedback unit. A battery powers the capacitive sensor 4, the microprocessor, and the feedback unit whenever the instrument is switched on. The microprocessor compares the output from the capacitive sensor 4 with a stored threshold value and activates the feedback unit whenever the threshold is exceeded. The nature, connection, and operation of the battery, the microprocessor, and the feedback unit are conventional and therefore not shown.

Figure 2:
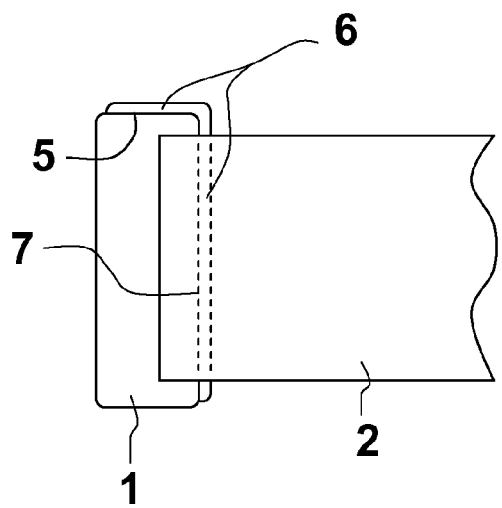
FIG. 2 shows a side view of an alternative embodiment of the posture assessment instrument without the capacitive sensor, where a pressure-sensitive foil is attached to the top and back of the housing.

An alternative embodiment is shown in FIG. 2, where a pressure-sensitive foil 6 is used instead of a capacitive sensor. The pressure-sensitive foil 6 is attached to the top 5 and the back 7 of the housing 1, where the contact area with the body of a user will increase when the body bends toward the housing 1.

Figure 3:
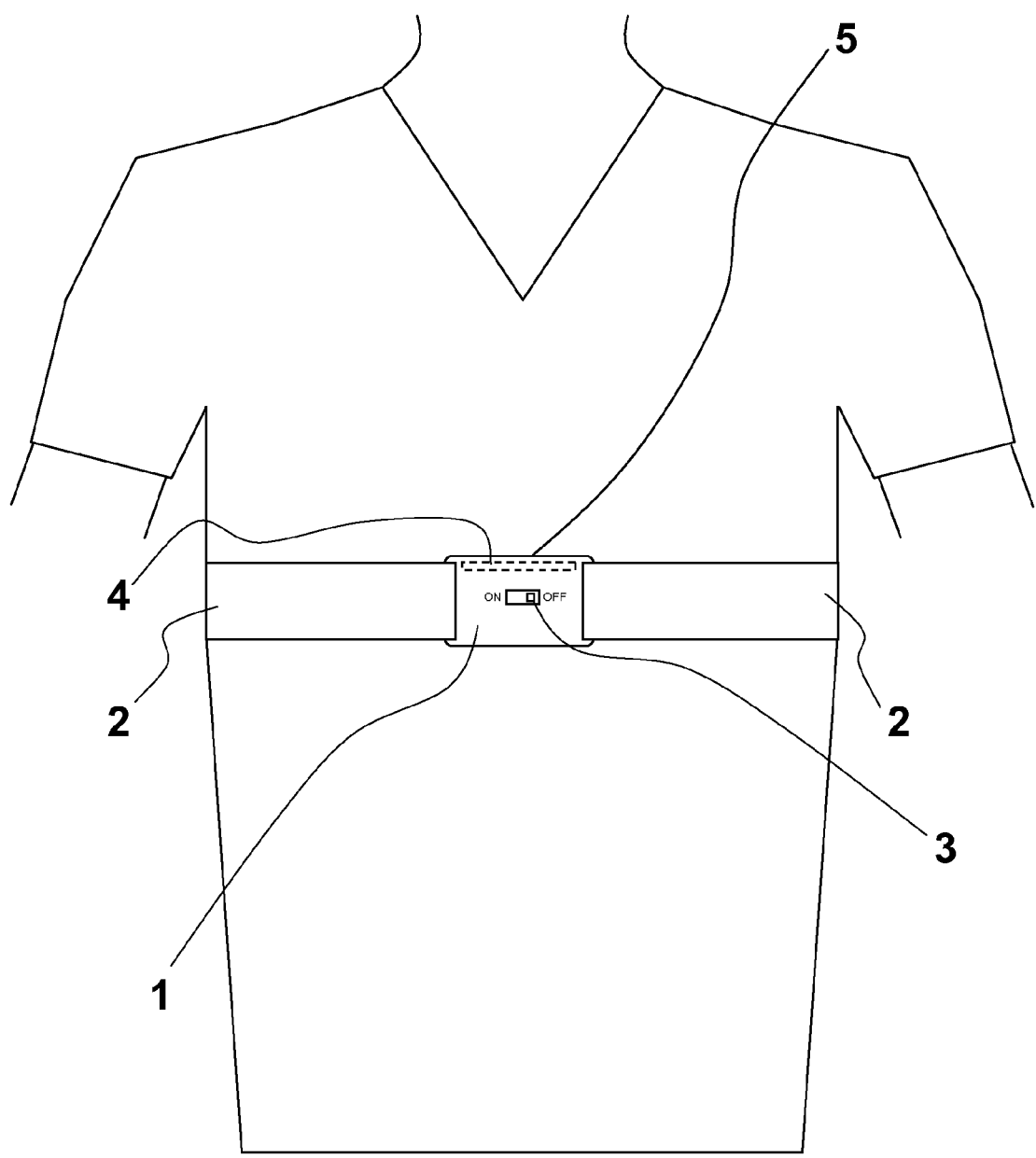
FIG. 3 shows a front view of a user with the posture assessment instrument strapped to the xyphoid area with a belt on top of a t-shirt.
Figure 4:
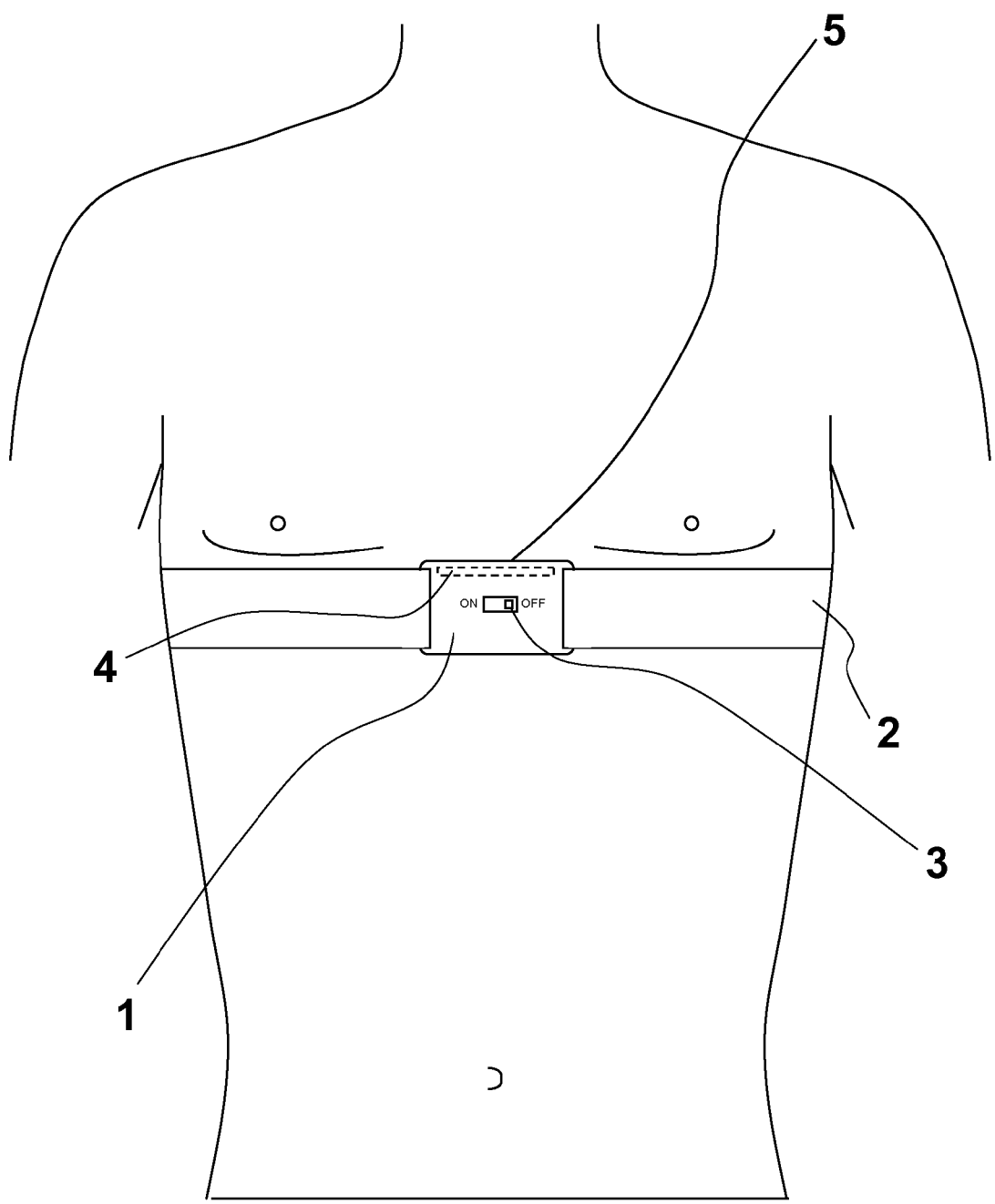
FIG. 4 shows a front view of a user with the posture assessment instrument strapped directly to the skin of the xyphoid area with a belt.

In order to assess slumped posture with either the preferred or the alternative embodiment, the housing 1 is strapped around the chest of a user with the belt 2, so that the housing is pressed against the xyphoid area. This can be done over a t-shirt as shown in FIG. 3 or directly on the skin as shown in FIG. 4. When viewed from the side, it can be seen that with an erect posture as in FIG. 5A, the distance between the top of the housing 5 and the body tissue of the chest is wider than when the user slumps as shown in FIG. 5B. Thus, the output of the capacitive sensor 4 situated just beneath the top of the housing 5 will vary accordingly.

Operation

The posture assessment and feedback instrument is used as follows:

The Instrument is strapped to the xyphoid area as shown in FIG. 3, FIG. 4, FIG. 5A, and FIG. 5B.

The user slumps to the point starting at which he or she wants to receive feedback. Remaining in this posture the user moves the switch 3 from the off-position to the on-position. The initial sensor output that follows is stored by the microprocessor as threshold value.

Whenever the user slumps far enough for the sensor output to exceed the stored threshold value, the microprocessor activates the feedback unit and causes it to generate a feedback signal. The feedback signal reminds the user to straighten up.

As soon as the posture has been corrected to the point where the sensor output drops below the stored threshold value, the feedback signal stops.

Summary, Ramification, and Scope

The posture assessment and feedback instrument of the present invention provides an inexpensive and user-friendly method of posture assessment and feedback, offering the following advantages:

Utilizing the proximity of a user's body as input variable makes a separate signal source with moveable hardware components redundant, thus facilitating production, cleaning, and handling of the instrument.

Having a sensor free of moveable components within a protective housing improves its durability.

Allowing an optional application to the clothes facilitates the operation and the demonstration of the instrument and reduces the formation of sweat in between the instrument and the body.

The fact that the capacitive sensor will work even when mounted within a plastic housing allows a wireless embodiment of a posture feedback instrument where all required electronic components are contained within a single housing. This wireless single housing type of posture feedback instrument is inexpensive, durable, and user-friendly.

Another user-friendly aspect of the present invention is its application to the xyphoid area, where it can be reached and handled by a user, while not being in the way when using a back rest.

Although the description above contains a number of specificities, these should not be construed as limiting the scope of the invention, but as merely providing illustration of the presently preferred embodiment of this invention.

For Example:

the described method for the prevention of postural slump could also be applied to prevent excessive rotation or lateral flexion of the spine;

the described method could also be applied to assess the bending of peripheral joints such as the wrist, elbow or knee;

the shape and location of the housing could be modified. When applied to the xyphoid area for slump-feedback, it could for example be extended or moved further under the pectoral muscle, where even more soft tissue will cover the top of the housing when the user slumps;

the shape and location of the sensor within the housing could be modified;

the housing could be applied to the body by means other than a belt.

Thus, the scope of the invention should be determined by the appended claims and their legal equivalents, rather than by the examples given.

I claim:

1. A method for posture assessment comprising the steps of:
   choosing a sensing means that provides an output in response to a distance between said sensing means and the body of a user,
   choosing a suitable area of said body having properties causing said distance to vary in response to a defined posture change, and
   applying said sensing means to said suitable area causing said distance and thus said output to vary in response to said defined posture change,
   whereby no separate signal source and no moveable hardware components are required, thus allowing said sensing means to be durable, cleanable, and usable, and
   whereby said user has the user-friendly choice of applying said sensing means either directly to the skin or to the clothing.

2. The method of claim 1 wherein said sensing means is capacitive.

3. The method of claim 1 wherein said output is compared to a stored threshold value and triggers a feedback signal when said threshold is exceeded.

4. The method of claim 1 wherein said defined posture change is spinal.

5. The method of claim 1 wherein said defined posture change is a change in spinal curvature.

6. The method of claim 1 wherein said defined posture change is slumping.

7. The method of claim 1 wherein said sensing means and all other electronic components required in the process of posture assessment are contained within a single housing.

8. A method for posture assessment comprising the steps of:
   choosing a sensing means whose signal output changes in response to changes of a contact area between said sensing means and the body of a user wearing said sensing means,
   choosing a suitable location on said body having properties causing said contact area to vary in response to a defined posture change, and
   applying said sensing means to said suitable location, causing said contact area and thus said output signal to vary in response to said defined posture change,
   whereby no separate signal source and no moveable hardware components are required, thus allowing said sensing means to be durable, cleanable, and usable, and
   whereby said user has the user-friendly choice of applying said sensing means either directly to the skin or to the clothing.

9. The method of claim 8 wherein said sensing means is pressure-sensitive.

10. The method of claim 8 wherein said output is compared to a stored threshold value and triggers a feedback signal when said threshold is exceeded.

11. The method of claim 8 wherein said defined posture change is a change in spinal curvature.

12. The method of claim 8 wherein said defined posture change is slumping.

13. The method of claim 8 wherein said sensing means and all other electronic components required in the process of posture assessment are contained within a single housing.

14. A method for posture feedback comprising the steps of:
    choosing a sensing means that provides an output in direct response to a distance between said sensing means and the body of a user,
    choosing a suitable area of said body having properties causing said distance to vary in response to postural slumping, and
    applying said sensing means to said suitable area causing said distance and thus said output to vary in response to said postural slumping, and
    comparing said output to a stored threshold value and triggering a feedback signal when said threshold is exceeded,
    whereby no separate signal source and no moveable hardware components are required, thus allowing said sensing means to be durable, cleanable, and usable, and
    whereby said user has the user-friendly choice of applying said sensing means either directly to the skin or to the clothing.

15. The method of claim 14 wherein said sensing means is capacitive.

16. The method of claim 14 wherein said sensing means and all other electronic components required in the process of posture assessment are contained within a single housing.

* * * * *